United States Patent [19]
Griffith et al.

[11] Patent Number: 5,853,373
[45] Date of Patent: Dec. 29, 1998

[54] BI-LEVEL CHARGE PULSE APPARATUS TO FACILITATE NERVE LOCATION DURING PERIPHERAL NERVE BLOCK PROCEDURES

[75] Inventors: Richard Lee Griffith, Allendale; Robert J. Strowe, Ramsey, both of N.J.; Jonathan C. Newell, Glenmont; Peter M. Edic, Albany, both of N.Y.; Ralph F. Messina, Belleville; Frederick Charles Houghton, Sussex, both of N.J.

[73] Assignee: Becton, Dickinson and Company, Franklin Lakes, N.J.

[21] Appl. No.: 695,151

[22] Filed: Aug. 5, 1996

[51] Int. Cl.⁶ ........................................................ A61B 5/05
[52] U.S. Cl. ............................................. 600/554; 607/116
[58] Field of Search ................................... 600/373, 554, 600/546, 547, 587; 607/115–117, 119, 46; 606/44; 604/272, 239

[56] References Cited

U.S. PATENT DOCUMENTS

| | | | |
|---|---|---|---|
| 3,313,293 | 4/1967 | Chesebrough et al. | 600/373 |
| 3,682,162 | 8/1972 | Colyer | 600/373 |
| 4,291,705 | 9/1981 | Severinghaus et al. | 600/554 |
| 4,387,723 | 6/1983 | Atlee, III et al. | 600/554 X |
| 4,515,168 | 5/1985 | Chester et al. | 600/554 |
| 5,092,344 | 3/1992 | Lee | 600/554 |
| 5,284,154 | 2/1994 | Raywond et al. | 600/587 |
| 5,306,236 | 4/1994 | Blumenfeld et al. | 600/546 X |
| 5,549,656 | 8/1996 | Reiss | 600/546 X |

FOREIGN PATENT DOCUMENTS 1526642  12/1989  Russian Federation ............... 600/554

Primary Examiner—Francis J. Jaworski
Attorney, Agent, or Firm—Arthur D. Dawson

[57] ABSTRACT

An electrolocation apparatus is provided for locating a nerve to which anesthesia may be delivered. The apparatus includes a needle assembly having an electrically conductive needle cannula non-conductive tube secured over the needle cannula, and a conductive plating on the tube. The conductors are connected to a stimulator that generates alternating high and low charge pulses with a constant low current level. The high charge pulses generate noticeable muscle twitches immediately after insertion of the needle into the patient. Muscle twitches responsive to the high charge pulses will peak in magnitude, and muscle twitches responsive to the low charge pulses will become observable as the needle approaches the targeted nerve, and will be indistinguishable from the muscle twitches responsive to the high charge pulses when the needle is in a position for administration of anesthetic.

7 Claims, 5 Drawing Sheets

5,853,373

BI-LEVEL CHARGE PULSE APPARATUS TO FACILITATE NERVE LOCATION DURING PERIPHERAL NERVE BLOCK PROCEDURES

BACKGROUND OF THE INVENTION

1. Field of the Invention

The subject invention relates to an apparatus for efficiently locating a nerve and for subsequently delivering an anesthetic to the nerve.

2. Description of the Prior Art

Many medical procedures require a patient to be at least locally anesthetized. A regional anesthesia or nerve block offers advantages over general anesthesia for many medical procedures. For example, a regional anesthesia or nerve block typically is less traumatic to the patient undergoing surgery and often permits a shorter post-operative recovery.

A regional anesthesia or nerve block necessarily requires location of the nerve to which anesthetic agent will be administered. The prior art includes methods for locating the nerve. In most such prior art methods, the doctor typically uses general knowledge of physical anatomy to approximately locate the targeted nerve. In accordance with one prior art method, an electrically conductive pad is positioned on the skin on a portion of the patient's body at some distance from the targeted nerve. For example, if the targeted nerve is in the shoulder, the electrically conductive pad may be secured to a distal portion of the arm. The electrically conductive pad is connected by a wire to a prior art stimulator box that is capable of generating electrical current, as explained further herein. An electrically insulated needle cannula with an uninsulated conductive tip is then urged through the skin and subcutaneous tissue in the general direction of the nerve to be anesthetized. The prior art needle is connected by a wire to the prior art electrical stimulator box.

The prior art stimulator box is electrically powered and is operative to produce an adjustable current pulse for a duration of approximately 100–200 microseconds ("uS"). The current pulse is set initially to a level of approximately 1.0–5.0 milliamps ("mA"). This current level typically is sufficient to stimulate the targeted nerve when the needle has been placed into the tissue in the approximate area of the targeted nerve. The stimulation will cause a noticeable muscle twitch on areas of the body controlled by the targeted nerve (e.g., the fingers). The current then is decreased slowly until the twitching disappears. The prior art needle then is advanced slowly toward the targeted nerve until the twitching reappears. This iterative procedure continues until the prior art needle is able to generate noticeable muscle twitches at a current level of approximately 0.2–0.3 milliamps. At this point, the prior art needle is considered to be sufficiently close to the targeted nerve for administration of the anesthetic agent. The anesthetic agent then is delivered directly through the needle while the needle continues to produce the current pulses. Cessation of the muscle twitch typically is considered to indicate successful location of the nerve.

The prior art electrolocation procedure is intended to ensure accurate placement of a needle for delivery of anesthetic. However, the prior art device and the prior art procedure for electrolocation of a targeted nerve have several drawbacks. For example, the prior art electrolocation device, including the stimulator box, is a fairly large, costly and reusable piece of equipment that is not easily sterilized. Thus, there are problems with using the prior art electrolocation device in the sterile environment of an operating room. It is typically necessary to employ two technicians for carrying out this prior art procedure, namely a first technician operating under sterile conditions and manipulating the needle, and a second technician spaced from the first technician and operating under non-sterile conditions to incrementally decrease the current level. The use of two technicians necessarily requires fairly high costs and requires considerable coordination and communication between the two technicians.

Second, the prior art electrolocation device does not provide a definitive indication of when the needle is properly positioned for injecting the anesthetic. The attending physician must rely upon judgment and experience to determine when the needle is in the optimum position.

Third, the considerable distance between the insulated needle and the prior art conductive pad requires the generation of a relatively high voltage to achieve the desired current level. A voltage of at least 25 volts ("V") is common in the prior art electrolocation apparatus. These relatively high voltage levels limit the use of the prior art apparatus. For example, the high voltage levels can affect the performance of pacemakers and other implanted electronic devices. Hence, the prior art electrolocation device generally cannot be used on patients with implanted electronics.

Additionally, the relatively high energy creates the risk of arcing. Hence the prior art electrolocation apparatus cannot be employed in many surgical environments, such as those where oxygen is being used, due to the risk of fire or explosion. The high current levels may also create the potential for tissue damage in proximity to the needle.

SUMMARY OF THE INVENTION

The subject invention is directed to an electrolocation apparatus for accurately and efficiently locating a nerve to which an anesthetic agent may be administered. The apparatus employs sufficiently low energy levels to avoid potential tissue damage and to permit use of the apparatus in situations where a patient has an implanted electronic device. The apparatus also is sufficiently small and inexpensive to be manufactured for single use and can be made sufficiently sterile for use in the sterile field of an operating room. Furthermore the apparatus can be used by only a single technician.

As noted above, the voltage required for an electrolocation apparatus is a function of the distance between two conductors and the contact resistance to the patient. To substantially minimize the distance, the subject invention provides both conductors on the needle cannula. More particularly, the electrolocation apparatus of the subject invention may employ a needle assembly having a pair of coaxially disposed conductors. An inner conductor of the pair of coaxial conductors may be defined by the needle. A non-conductive sheath or tube may then be mounted over the inner conductor and may be plated, coated, coextruded or otherwise provided with an electrically conductive material, which functions as the outer conductor. A bevel or chamfer may be defined at the distal end of the non-conductive tube. The bevel may be defined by a non-conductive adhesive at the distal end of the tube. The beveled adhesive functions to hold the tube in place and also facilitates entry of the needle assembly into the patient. The spacing between the conductors of the electrolocation device is defined by the distance from the distal edge of the bevel to the conductive sheath, which preferably is slightly more than 1.0 millimeter ("mm"). In view of this very small distance, a very low voltage can be used to generate the required current. It is believed by the inventors herein that this aspect of the invention makes the subject electrolocation apparatus suitable for use with patients having implanted electronic devices, such as pacemakers. Furthermore, the low energy level permits the subject electrolocation apparatus to be used in virtually all operating room environments, including those where prior art electrolocation apparatus had created the potential for combustion. Additionally the low voltage permits simple electronic circuitry that can be provided conveniently in a small package.

As noted above, the prior art electrolocation device had required two technicians, namely a first technician to carefully manipulate the needle and a second technician to carefully vary the current level. The subject electrolocation apparatus employs entirely different structure that operates under entirely different principles, and enables use of the subject electrolocation apparatus by a single technician. The electrolocation apparatus takes advantage of the determination that the threshold electrical parameter for generating a muscle twitch is measured more accurately in terms of electrical charge rather than electrical current. Electrical charge is the product of current and time, and charge can be varied by changing either the current level or the time duration. In a first preferred embodiment, the subject electrolocation apparatus generates constant current pulses; however, the sequential pulses alternate between a relatively long duration and a relatively short duration. In this manner, sequential constant current pulses alternate between the relative high charge and a relatively low charge. In a second embodiment, the electrolocation apparatus is operative to alternately deliver relatively high current pulses (e.g., 0.5 mA) and relatively low current pulses (e.g., 0.1–0.2 mA). Each pulse may be of the same duration (e.g., 0.1–0.2 milliseconds ("mS") and the pulses may be generated at uniform intervals (e.g., 0.25–2.0 seconds).

One approach to using the electrolocation device of the subject invention may include urging the needle into the patient and toward the targeted nerve. The relatively high charge pulses will generate muscle twitches at a location distant from the nerve after the skin has been penetrated (e.g., when the tip of the needle is about 1.0 cm from the targeted nerve). The relatively low charge pulses, however, will not produce a sufficient charge to generate muscle twitches at this initial distance. The pulses may be separated, for example, by approximately one-half second (hereafter, "½" or "0.5"second(s)). Thus, the physician initially will observe muscle twitches at intervals of approximately one second, coinciding with the high charge pulses.

As the needle is moved toward the targeted nerve, the physician may observe a slight increase in the magnitude of the initially observed muscle twitches caused by the high charge pulses. Simultaneously, the physician will begin to observe small muscle twitches in response to the low charge pulse that follows each high charge pulse. Thus, using the preceding example, the physician will observe a large twitch in response to a high charge pulse followed 0.5 seconds later by a smaller twitch in response to a low charge pulse and then followed 0.5 seconds later by another larger twitch in response to a high charge pulse.

Twitches generated in response to the high charge pulses will quickly reach a peak, such that further movement of the needle toward the targeted nerve will not significantly increase the magnitude or severity of twitches resulting from high charge pulses.

Twitches generated in response to low charge pulses gradually will increase in magnitude and intensity as the needle continues to approach the targeted nerve. These changes in the magnitude and intensity of the low charge twitches will be readily observable by the physician inserting the needle. As the tip of the needle approaches the targeted nerve, the major and minor twitches will become substantially indistinguishable, and the physician will merely observe substantially identical muscle twitches at intervals of approximately 0.5 seconds or twice the interval initially observed. This will indicate to the physician that the tip of the needle is properly positioned for administration of the specified anesthetic. The anesthetic agent may then be urged through the needle and to the targeted nerve. The anesthetized nerve will then stop twitching, thereby giving the physician a clear indication that the targeted nerve has been reached and that the anesthetic has had its intended effect. The physician may then merely trigger a switch on the small control of the electrolocation apparatus to terminate the flow of current to the needle.

While principally described herein with the concept of generating sequentially alternating charge pulses of high and low levels, it will be appreciated by the skilled artisan that the construction of the electrolocation device and components described herein can be configured to produce a repeating pattern of graded charge pulses depending on the application desired. For instance, depending upon the anatomy of the region surrounding the nerve being sought, it may prove beneficial to have a repeating pattern of gradual decrease in charge pulse as the nerve is approached, rather than an alternating series of absolute high and low level charge pulses as the nerve is approached. That is to say, the apparatus and associated compnents can be configured such that rather than delivering an alternating series of high and low level charge pulses, it will deliver a repeating pattern of graded charge pulses, with the grade in each pattern declining from a selected maximum level charge pulse to a selected minimum level charge pulse. In this manner, for certain anatomies, the practitioner is provided with a greater range of clinical observations respective of nerve reaction to the charge pulses, thereby providing more accurate knowledge to the practitioner of the location of the apparatus to the nerve. Other patterns are also possible.

DETAILED DESCRIPTION OF THE PREFERRED EMBODIMENT

Figure 1:
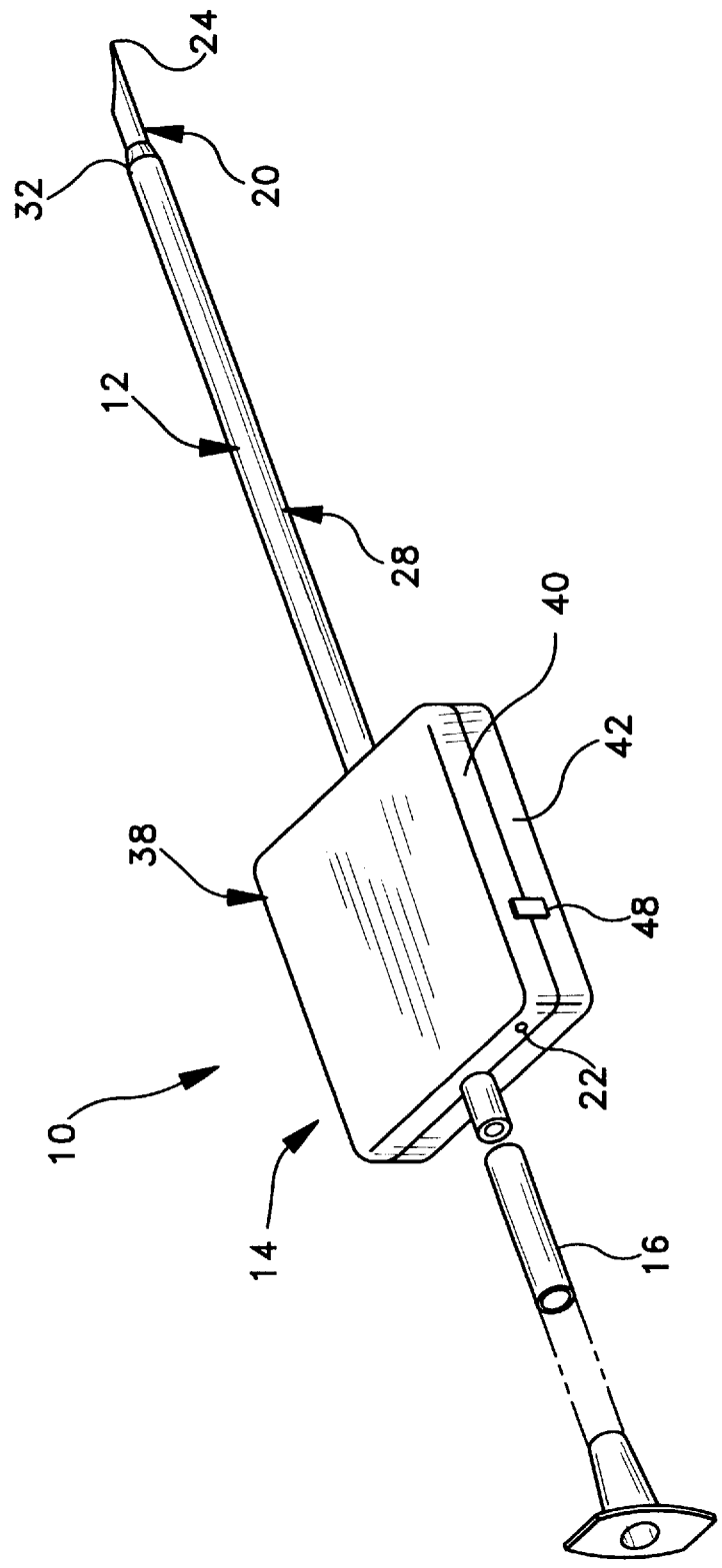
FIG. 1 is a perspective view of a bipolar electrolocation apparatus in accordance with the subject invention.

An electrolocation apparatus in accordance with the subject invention is identified generally by the numeral 10 in FIG. 1. The apparatus 10 includes a needle assembly 12, a stimulator 14 and a tube 16 for delivering a dose of anesthetic through needle assembly 12.

Figure 2:
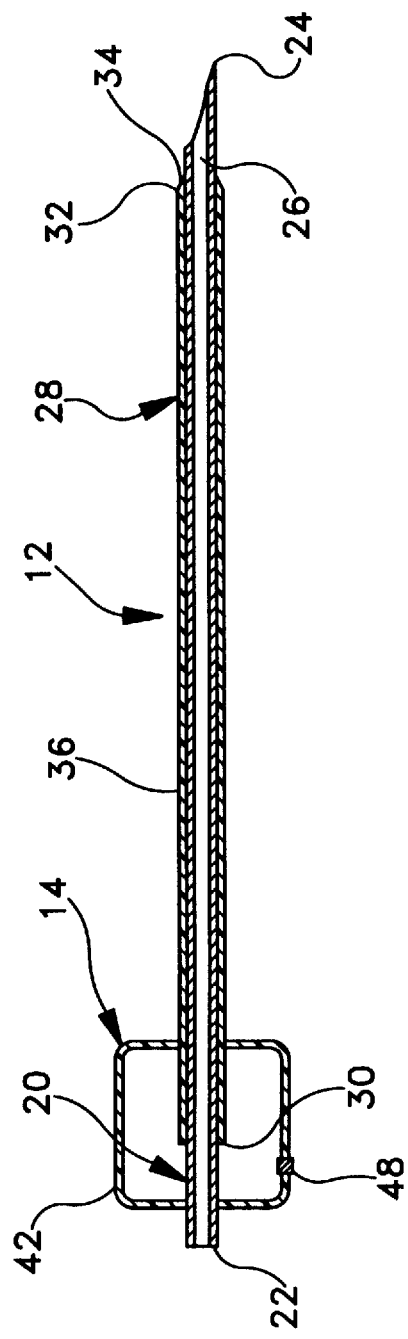
FIG. 2 is a cross-sectional view of a needle in accordance with the subject invention.

Needle assembly 12, as shown more clearly in FIG. 2, includes an elongate needle cannula 20 having opposed proximal and distal ends 22 and 24 and a lumen 26 extending continuously therebetween. Needle cannula 20 is formed from an electrically conductive material and preferably stainless steel. Proximal proportions of needle cannula 20 are securely mounted in stimulator 14 with proximal and distal ends of needle cannula 20 being on opposite sides of stimulator 14. Distal end 24 of needle cannula 20 is beveled to a point that facilitates piercing of tissue for accessing the targeted nerve.

Needle assembly 12 further includes a thin walled tube 28 coaxially disposed over needle cannula 20. Tube 28 has opposed proximal and distal ends 30 and 32 respectively, and is formed from a non-conductive material, such as polyimide. Proximal end 30 of tube 28 is disposed in stimulator 14 as explained further herein. Distal end 32 of tube 28 is spaced proximally from bevelled distal end 24 of needle cannula 20. Tube 28 is dimensioned to be closely engaged against the outer cylindrical surface of needle cannula 20. However, secure retention of tube 28 on needle cannula 20 is achieved by a non-conductive epoxy 34 or other such adhesive extending between distal end 32 of plastic tube 28 and the outer cylindrical surface of needle cannula 20. Epoxy 34 is chamfered to facilitate entry of needle assembly 12 into a patient. The chamfer preferably defines a length of about 1.0 mm.

Tube 28 includes a conductive layer 36 on its outer cylindrical surface which may be applied by plating or coating. Layer 36 preferably is gold and extends continuously from proximal end 30 to distal end 32 of tube 28 at a thickness of approximately 550 Angstroms. Needle assembly 12 effectively functions as a pair of coaxial conductors as explained further herein. In particular, stainless steel needle cannula 20 functions as an inner conductor, while gold layer 36 on tube 28 functions as an outer conductor. Tube 28 defines a non-conductive insulating material separating the inner and outer conductors defined respectively by stainless steel needle cannula 20 and gold layer 36.

As noted above, stainless steel needle cannula 12 extends continuously through stimulator 14, such that proximal end 22 of needle cannula 20 is disposed on one side of stimulator 14, while distal end 24 is disposed on the opposed side thereof. Proximal end 30 of plastic tube 28 is disposed within stimulator 14. As a result, both stainless steel needle cannula 12 and gold layer 36 are exposed for electrical contact within stimulator 14.

Stimulator 14 includes a generally rectangular housing 38 which can have length and width dimensions, for example, of approximately 0.781 inch and a thickness dimension, for example, of approximately 0.375 inch. Housing 38 can be formed from two molded thermoplastic housing halves 40 and 42 that are welded or adhered to one another. Top and bottom walls respectively may include concave regions to facilitate gripping by the digits of the hand.

Housing 38 performs multiple functions, including providing structural support for needle assembly 12, providing a convenient grip for manipulation of needle assembly 12 and safely enclosing the electronic components of the electrolocation apparatus 10.

The electronic circuitry of stimulator 14 includes an on/off switch 48 and a light emitting diode (LED) 50 both of which are accessible and/or visible from the exterior of housing 38. On/off switch 48 functions to complete circuitry between a battery and other portions of the circuitry as described further below, and optionally may permit switching between high and low charge levels. LED 50 is operative to generate a pulse of light with each pulse of electrical energy so that the technician or attending physician can compare energy pulses with muscle twitches in the patient.

Figure 3:
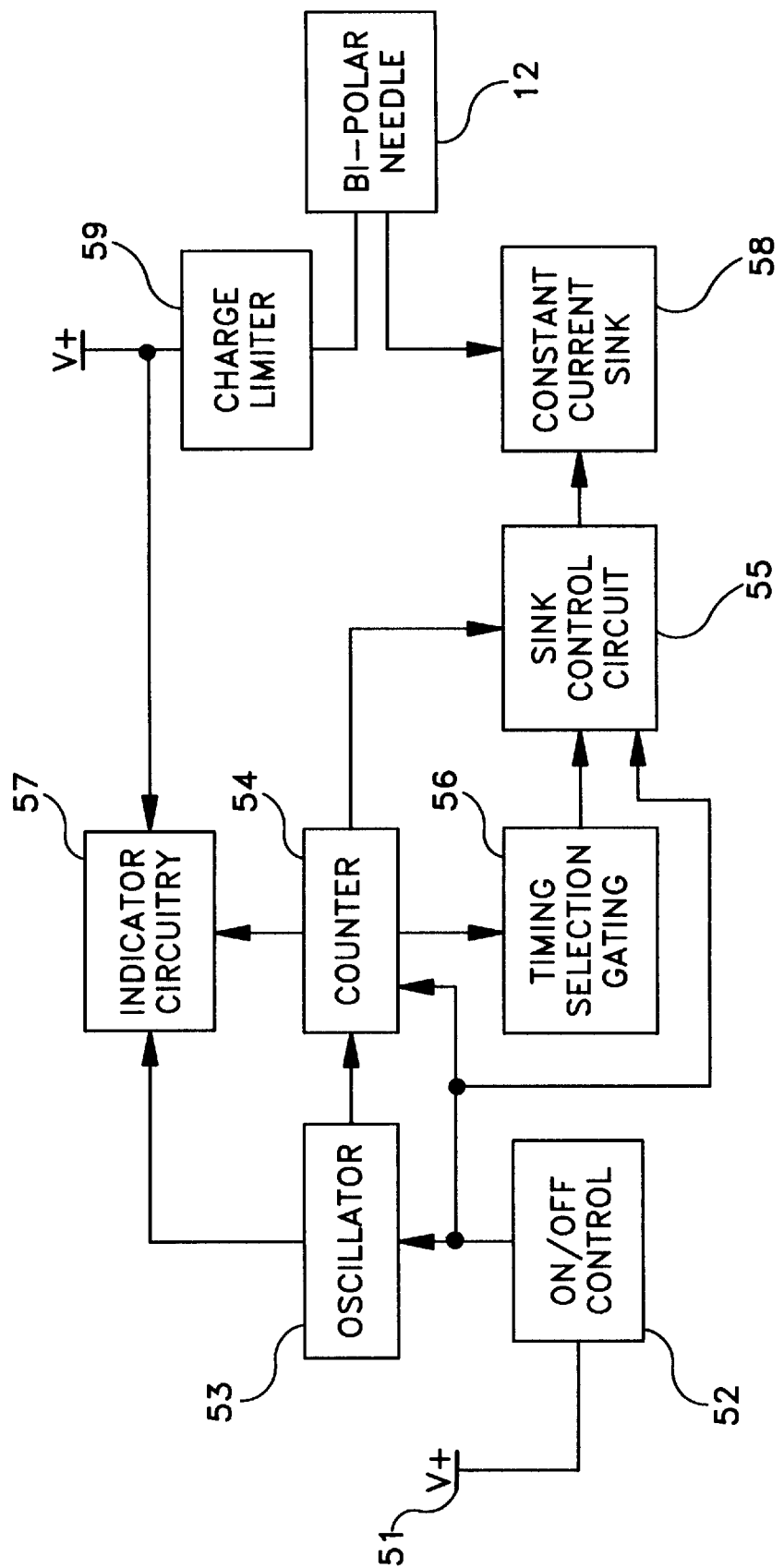
FIG. 3 is a block diagram of a set of circuit components which function to produce appropriate charge pulses across the needle of FIG. 2 in accordance with the subject invention.

FIG. 3 is representative of circuitry which can be used in stimulator 14. As the skilled artisan will appreciate, one way of implementing such circuitry is to digitize it, utilizing CMOS technology as active elements. Other implementations, such as custom integrated circuits ("ICs") are also possible. Here, on/off switch 48 is connected to a three-volt lithium cell battery 52. In the off state, the quiescent current is under 1 microamps ("uA"), providing a battery life in excess of eight years, and thereby ensuring adequate shelf life for the electrolocation apparatus 10. In the on state, the oscillator and counter described below are enabled, and the battery will operate stimulator 14 for approximately 100 hours.

Figure 5:
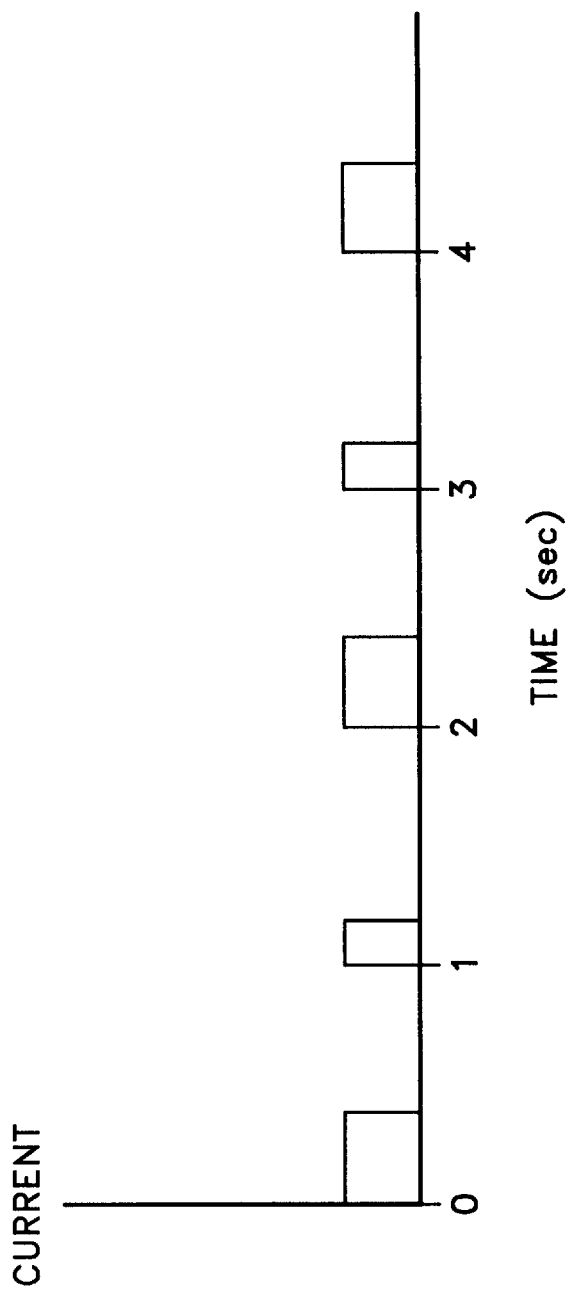
FIG. 5 is a graph showing a pulse generation pattern in accordance with the subject invention.

The time duration pulse modulation is achieved by a counter 54. Using the outputs of the counter 54, it is possible to generate a pulse as short as 122 uS. Since the outputs of the counter 54 are periodic signals, the Timing Selection Gating network 56 selects only one period of the output signal and applies it to the current source network 58. In the embodiment shown in FIG. 3, the gating network 56 may alternatively enable either one of a low charge pulse or one of a high charge pulse. As shown schematically in FIG. 5, stimulator 14 is operative to alternately generate short and long duration pulses. All of the pulses will be of a constant current, but will be of different durations. For example, stimulator 14 may be operative to generate a pulse at a current level of 0.2 mA for 122 uS to produce a relatively low charge of 24.4 nanocoulombs ("nC"), followed by a current pulse of 0.2 mA for approximately 488 uS to produce a relatively high charge of 97 nC. It will be realized by the skilled artisan that depending on the components selected to generate the pulses, the duration of the pulses may vary within a range of time, for example, of about +/−20% of the durations stated herein. Other paired pulses of constant current for different durations may be used to produce alternating low and high charges.

The circuit of FIG. 3 also is designed to optionally provide constant duration pulses with current amplitude modulation. For example a low current pulse of 0.2 mA may be generated for 122 uS to produce a relatively low charge of 24.4 nC and may be followed by a high current pulse of 0.8 mA for 122 uS to produce a relatively high charge of 97 nC. It will be noted that the charges produced by the current level modulation option equal the charges produced by the time duration modulation option.

Figure 4:
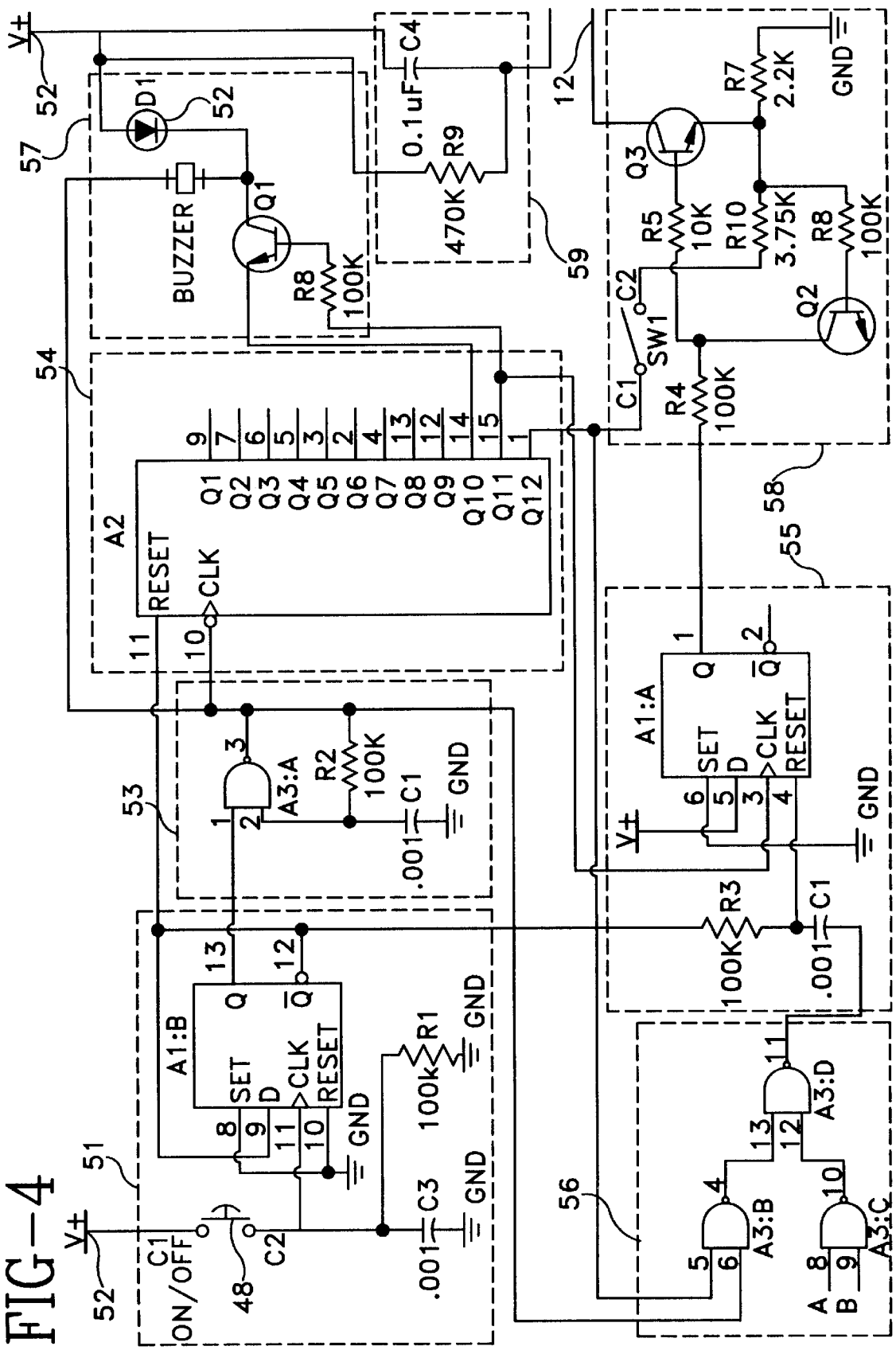
FIG. 4 illustrates an example of a combination of operative circuit components within the blocks of FIG. 3.

FIG. 3 is a block diagram of a set of circuit components, in stimulator 14, which function to produce appropriate charge pulses across bipolar needle 12, and FIG. 4 illustrates an example of a combination of operative circuit components within the blocks of FIG. 3. As seen in FIG. 3, an on/off control 51, actuated by switch 48, has an output that keys an oscillator 53 to activate a counter 54, and another output that enables and disables the counter 54. A third output is fed to a control circuit 55 which receives an output from the counter 54 and activates a constant current sink 58 coupled to one electrode (20 or 36) of the bipolar needle 12. Indicator circuitry 57, which drives LED 50, receives inputs from the oscillator 53, the counter 54, and the current source V+, which through a charge limiter 59 is coupled to the other electrode (36 or 20) of the bipolar needle 12. The timing and magnitude of the charge pulses are modulated by a Timing Selection Gating component 56 that is coupled to the control circuit 55.

Turning to the circuit details in FIG. 4, the on/off Control 51 may consist of the on/off switch 48 which couples the voltage V+ of battery 52 to circuitry including a flip-flop A1B and an RC (R1,C3) combination. When the apparatus 10 is to be used, the switch 48 is put in the on position and stays on to avoid any current surges at the needle. The flip-flop A1B controls the timing of the oscillator 53, which may comprise a Schmitt trigger A3A, and enables and disables the counter 54, which may be in the form of a 12-bit counter A2, and the sink control circuit 55, which may comprise a flip-flop A1A. When A1B is ON, output line 12 is low or 0, so the reset of counter A2 is off and thus it is free to count, and the reset of A1A is off so it is free to change state. Concomitantly, output line 13 of A1B is high or positive, so that the oscillator A3A operates, e.g., at 4.096 kilohertz ("kHz"), to cause counter A2 to count, whereupon pin 1 of A2 is caused to change state every ½ second and pin 15 goes positive every ½ second. Thus, pin 15 changes state at twice the rate of pin 1. When A1B is off, line 13 goes low, stopping the output of A3A, and line 12 goes high, resetting A2 and A1A.

When pin 15 of A2 goes positive, the clock signal to A1A causes output line 1 to go high, by voltage V+, supplying base current to transistor Q3, through resistors R4 and R5. Q3 is thereby caused to conduct closing a current path for current to flow through the needle 12 from the battery V+, across capacitor C4, and through resistor R7 to ground. If the voltage at R7 goes above 0.55V, the base of transistor Q2 will be driven through resistor R6 to turn Q2 on, which in turn drops the base current to Q3, thus maintaining the voltage across R7 at 0.55V. Accordingly, the current through the needle 12 is maintained substantially constant. In the event of a short or failure in the needle's current path, the capacitor C4 acts as a charge limiter by charging to a preselected maximum charge and limiting the current level.

The timing and form of the current pulses is determined through the use of the Timing Selection Gating component 56 which comprises three gates A3B, A3C, and A3D that receive inputs from the oscillator A3A and the counter A2 and provide an output to flip-flop A1A of the sink control circuit 55. Gate A3B controls the short pulses shown in the timing diagram of FIG. 5. It will be seen that input pin 10 to counter A2 works on negative pulses so that when the output of A3A, on pin 3, goes negative, output pin 15 of A2 goes positive driving A1A to turn on the current through the needle path as just explained above. The output on pin 3 of A3A is also supplied to input pin 6 of gate A3B, the other input pin 5 of which receives the output from pin 1 of A2. If the signal on pin 1 and in turn on pin 5 is high, A3B can function when pin 6 goes high. If pin 1 is low or at 0, then pin 5 is low and A3B cannot function. The operation of A3B can be used to control the alternating of the short and long charge pulses. When pin 1 is high, the short pulses will be produced.

More particularly, when pin 3 of A3A goes low, counter 54 will go to its next state. Pin 15 goes high so that current begins to flow through the needle and pin 1 is high so pin 5 of A3B is high, while pin 6 is low or 0 along with pin 3. The output of A3B on pin 4 will be 1, which is input on pin 13 to gate A3D. With a high input on pin 12, the output of gate A3D, on pin 11 will be 0. Now, when oscillator A3A outputs a high on pin 3, the counter A2 does not change its state, but pins 5 and 6 of A3B will both be high, so that the output on pin 4 will go to 0 causing the input to pin 13 to be 0. If the input on pin 12 is still high, the output of A3D on pin 11 goes high. The high signal on pin 11 is coupled through capacitor C2 to the reset of flip-flop A1A causing its output on pin 1 to got to 0, turning off the constant current sink 58 and the current through the needle 12. A short current pulse will then have been produced of 122 uS duration.

To produce the longer pulses, gate A3C is used and gate A3B is disabled. Since A3B can only function when pin 1 of A2 is high, the signal on pin 1 is caused to go low turning A3B off. In this condition the reset function of A1A is controlled only by A3C. The output of A3C may be controlled according to the pulse ratio table shown adjacent to A3C in FIG. 4. By appropriately connecting the A (8) and B (9) inputs of A3C to the listed combination of pins of counter A2, the time ratios between the short and long pulses shown in the left hand column of the table can be achieved, thus accomplishing pulse width modulation of the charge pulses.

For accomplishing pulse amplitude modulation, the A and B inputs to A3C can both be connected to pin 10 of A2 to produce a pulse time ratio of 1 to 1, the pulses being of 122 uS. A resistor R10 in the constant current sink 58 is connected into the circuit between pin 1 of A2 and the emitter of transistor Q3 by closing a switch SW1. When pin 1 is high, current flows through R10 and resistor R7 to ground. The current in the current path through the needle 12 is thus decreased since the voltage across R7 remains constant and the current through R7 is made up of two sources. Consequently, the magnitude of the current pulse across needle 12 becomes a comparatively low current pulse. When pin 1 of A2 is low, i.e., goes to ground, R10 is configured in parallel with R7 with respect to ground, so that the resistance across R7 and R10 drops with respect to the current path. Since the voltage of 0.55V is maintained at their junction point, as explained above, more current is needed across both resistors. Thus, the magnitude of the current pulse across the needle 12 is increased resulting in a comparatively high current pulse. Accordingly, pulse amplitude modulation can be accomplished with this circuitry.

If desired, both pulse width and pulse amplitude modulation can be produced by selection of the pulse ratios in the pulse ratio table and the switching of resistor R10 into the circuit.

Lastly, the indicator circuitry 57 is configured to activate whenever a pulse has been produced, irrespective of the modulation, and to produce a simple on or off indication. Thus, the LED 50 will flash ON upon the occurrence of a charge pulse or the buzzer 60 will produce a sound in accordance with the timing and state change of the outputs on pin 3 of A3A and pin 15 of A2.

As noted above, proximal end 22 of stainless steel needle cannula 20 projects entirely through housing 38 of stimulator 14. As shown in FIG. 1, proximal end 22 of stainless steel needle cannula 20 is connected to flexible tubing 16 which extends to a hub that is connectable to a syringe for delivering a selected dose of anesthetic. In an alternate embodiment, proximal end 22 of stainless steel needle cannula 20 may be mounted directly to a needle hub that is connectable to a syringe for administering a selected dose of anesthetic.

In use, an anesthesiologist or nurse anesthetist inserts the bevelled distal tip 24 of stainless steel needle cannula 20 into a patient and toward the targeted nerve. No conductive pad and no wires are used. In the constant current embodiment described herein, the switch 48 on the stimulator 14 is then actuated to generate the low constant current pulses of electrical energy. Proper functioning of the electrolocation apparatus 10 is confirmed by the flashing LED 50 generating a pulse of light concurrent with each respective pulse of energy. The respective pulses of energy are generated at ½ second intervals. The high charge pulses of 0.2 mA for 488 uS will generate a charge of 97 nC. The low charge pulses are of the same 0.2 mA current, but last for only 122 uS and will generate a charge of only 24.4 nC. The higher charge pulses of 97 nC will be sufficient to generate observable muscle twitches at a substantially superficial location after the skin has been penetrated by the gold layer 34, while the lower charges, pulses of 24.4 nC will not be sufficient to initially generate any observable muscle twitches at this distance from the nerve. Thus, the anesthesiologist or nurse anesthetist will observe muscle twitches at approximately one second intervals coinciding with the high charge pulses.

The needle assembly 12 is urged further toward the targeted nerve. This advancement of the needle assembly 12 will show a gradual increase in the magnitude of the twitches occurring at one second intervals. However, these twitches in response to the high charge will soon peak. The anesthesiologist or nurse anesthetist then will observe small magnitude muscle twitches between the larger magnitude twitches. Thus, alternating small and large magnitude twitches will be readily observable.

As the needle assembly 12 is further advanced into the patient, the small magnitude muscle twitches will increase in magnitude to approach the magnitude of the peaked large magnitude muscle twitches generated by the high charge pulses. As the distal tip 24 of the stainless steel needle cannula 20 nears the targeted nerve, the muscle twitches generated in response to the low charge pulses will be substantially indistinguishable from the muscle twitches generated in response to the high charge energy pulses. Thus, the anesthesiologist or nurse anesthetist will observe substantially identical muscle twitches at 0.5 second intervals. This readily observable response will indicate to the anesthesiologist or nurse anesthetist that the bevelled distal tip of needle cannula 20 is sufficiently close to the targeted nerve for administration of the anesthetic. The anesthetic is delivered in the conventional manner by actuation of the hypodermic syringe communicating with the proximal end 22 of stainless steel needle cannula 20.

The exact procedure can be carried out by the alternate embodiment which modulates current level.

While the invention has been described with respect to a preferred embodiment, it is apparent that various changes can be made without departing from the scope of the invention as defined by the appended claims. For example, the stimulator may have switch mechanisms for changing the current level or the pulse width to vary the respective levels of the charges delivered to the patient. Additionally, other indications of pulse generation may be provided, including an audible buzzer in place of or in addition to the LED described above.

What is claimed is:

1. An electrolocation apparatus comprising a needle cannula having opposed proximal and distal ends and a lumen extending therebetween, said needle cannula being formed to define first and second conductors electrically insulated from one another; and a stimulator connected to the respective conductors on the needle cannula and operative to generate high and low charge pulses of electrical energy, and wherein said stimulator comprises a current source coupled to one of said respective conductors on said needle cannula;

path means, connected between the other of said respective conductors on said needle cannula and ground, for completing a current path passing through said needle cannula;

pulsing means, connected to said path means, for turning said current on and off to produce charge pulses through said needle cannula, said pulsing means comprising:

a transistor, connected between said needle cannula and said path means, for controlling charge conduction in said current path and through said needle cannula;

gating means, coupled to the base of said transistor, for providing base current thereto for turning conduction through said transistor on and off; counter means, connected to said gating means, for determining the timing of the base current provided to said transistor by said gating means; and means for controlling said counter means to regulate the timing of said base current in turning conduction of said transistor on and off to produce alternating high and low charge pulses across said needle cannula.

2. The electrolocation apparatus of claim 1, wherein said path means comprises constant current means for maintaining the current through said path and said needle cannula at a preselected level.

3. The electrolocation apparatus of claim 2, wherein said constant current means comprises:

a resistor connected to a point between said transistor and ground; and a second transistor connected between the base of said transistor and ground and having its base resistively coupled to said point.

4. The electrolocation apparatus of claim 3, further comprising means for regulating the amplitude of said charge pulses including a second resistor connected between said counter means and said point.

5. The electrolocation apparatus of claim 1, further comprising charge limiting means, comprising a capacitor coupled between said current source and said one of said respective conductors, for limiting the level of charge that can pass through said needle cannula.

6. The electrolocation apparatus of claim 1, wherein said means for controlling said counter means comprises:

a first gate means having its output coupled to said counter means and said gating means;

a first flip-flop means coupled to said first gate means and said counter means; and on/off switch means for controlling the activation of said first flip-flop means.

7. The electrolocation apparatus of claim 6, wherein said gating means comprises:

a second flip-flop having an output resistively coupled to the base of said transistor;

a second gate means having its output coupled to an input of said second flip-flop;

a third gate means having its output connected to an input of said second gate means and its inputs connected to an output of said counter means; and a fourth gate means having its output connected to an input of said second gate means and one input connected to an output of said counter means and another input connected the output of said first gate means.

* * * * *